(12) United States Patent
Tsuji et al.

(10) Patent No.: US 6,808,516 B2
(45) Date of Patent: Oct. 26, 2004

(54) DISPOSABLE WEARING ARTICLE (75) Inventors: Tomoko Tsuji, Kagawa-ken (JP); Takako Uosawa, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 390 days.

(21) Appl. No.: 10/109,187

(22) Filed: Mar. 28, 2002

(65) Prior Publication Data

US 2002/0143313 A1 Oct. 3, 2002

(30) Foreign Application Priority Data

Apr. 2, 2001 (JP) ...................................... 2001-103961

(51) Int. Cl.[7] .............................................. A61F 13/15
(52) U.S. Cl. ............................................... 604/385.25
(58) Field of Search ........................ 604/385.24–85.31

(56) References Cited

U.S. PATENT DOCUMENTS 5,449,353 A * 9/1995 Watanabe et al. ...... 604/385.27
5,876,392 A * 3/1999 Hisada ................... 604/385.29
5,940,887 A * 8/1999 Rajala et al. ................. 2/243.1
5,947,947 A   9/1999 Endres et al.
6,168,585 B1   1/2001 Cesco-Cancian
6,179,820 B1   1/2001 Fernfors
6,595,976 B2 * 7/2003 Jitoe et al. ............. 604/385.29

FOREIGN PATENT DOCUMENTS

EP        0 904 753        3/1999
JP        9-75390          3/1997

* cited by examiner

*Primary Examiner*—John J. Calvert
*Assistant Examiner*—C. Lynne Anderson
(74) *Attorney, Agent, or Firm*—Butzel Long (57) ABSTRACT

A disposable wearing article has a pad member provided a pair of elastic thigh-tightening bands lying on transversely opposite side edges thereof. Front ends of first free zones and rear ends of second free zones of the respective elastic thigh-tightening bands are connected to the transversely opposite side edges in the vicinity of a waist-hole of pant member so that middle zones and first and second free zones of these thigh-tightening bands extend generally parallel to the respective leg-holes so as to substantially form loops.

4 Claims, 6 Drawing Sheets

DISPOSABLE WEARING ARTICLE

BACKGROUND OF THE INVENTION

This invention relates to a disposable wearing article for absorption and containment of bodily discharges.

Japanese Patent Application No. 1997-75390A discloses a disposable wearing article comprising pants composed of front and rear waist regions and a crotch region extending therebetween and transversely opposite side edge portions of these waist regions put flat and joined together to define a waist-hole and a pair of leg-holes, and a body fluid absorbent pad which has a liquid-pervious topsheet, a liquid-impervious backsheet and a liquid-absorbent core disposed between these two sheets and which is attached to the inner side of the pants and extending on the crotch region into the front and rear waist regions.

The front and rear waist regions of the pants are provided in transversely middle zones on respective inner sides with flexible suspender members extending from peripheral edge of the waist-hole toward the crotch region. The respective suspender members are formed at desired zones thereof with first fastener zones having stiffness higher than the suspender members. The pad is formed, on the other hand, on its front and rear end portions with second fastener zones having a stiffness higher than those of the top- and backsheets constituting the pad and adapted to be securely engaged with the first fastener zones. The second fastener zones of the pad may be securely engaged with the first fastener zone of the pants to attach the pad to the inner side of the pants before the article is put on a wearer's body.

With the article disclosed in the above-cited Application, the pad itself is not fixed to a wearer's crotch region and, in addition, the region of the pad except the second fastener zones is free to move relative to the pants. As a result, the pad easily moves back-and-forth and particularly right- and leftward in a wearer' crotch region. As the pad is apt to move readily from its desired position in the crotch region, bodily discharges such as urine and feces which should be absorbed and contained in the pants are likely to leak from the pants in the wearer's crotch region.

SUMMARY OF THE INVENTION

It is an object of this invention to provide a disposable wearing article improved so that a pad is not easily displaced from its proper position in the wearer's crotch region and able to prevent bodily discharges from leaking out from the wearing article in a wearer's crotch region.

According to this invention, there is provided a disposable wearing article comprising a pant member composed of front and rear waist regions opposed to each other and a crotch region therebetween wherein transversely opposite side edge portions of the waist regions overlaid and joined together so as to define a waist-hole and a pair of leg-holes, and a body fluid absorbent pad member lying inside the pant member and extending from the crotch region into the front and rear waist regions.

Further, the pad member has front and rear ends and transversely opposite side edges and a pair of elastic thigh-tightening bands. The thigh-tightening bands respectively have middle zones lying in the crotch region of the pant member and connected to side edges of the pad member, first free zones lying on a side of a front end of the pad member and extending toward side edges of the waist region and second free zones lying on a side of a rear end of the pad member and extending toward the side edges of the waist region. Front ends of the first free zones and rear ends of the second free zones are connected to the side edges of the waist region in vicinity of the leg-holes of the pant member while the middle zones and first and second free zones of the thigh-tightening bands extend generally parallel to the respective leg-holes of the pant member so as to substantially form loops.

This invention includes the following preferred embodiments: The front and rear ends of the pad are connected to the front and rear waist regions of the pant member.

The pad member has a pair of elastic first suspender bands extending from both sides of its front end toward the side edges of the waist region and a pair of elastic second suspender bands extending from both sides of its rear end toward the side edges of the waist region, and front ends of the first suspender bands and rear ends of the second suspender bands are connected to the side edges of the waist region in vicinity of the waist-hole of the pants portion.

The pant member is formed of a substantially liquid-impervious sheet and the pad is formed of a liquid-pervious topsheet, a liquid-impervious backsheet and a liquid-absorbent core interposed between these two sheets.

DETAILED DESCRIPTION OF THE PREFERRED EMBODIMENTS

Details of a disposable wearing article according to this invention will be more fully understood from the description given hereunder in reference to the accompanying drawings.

Figure 1:
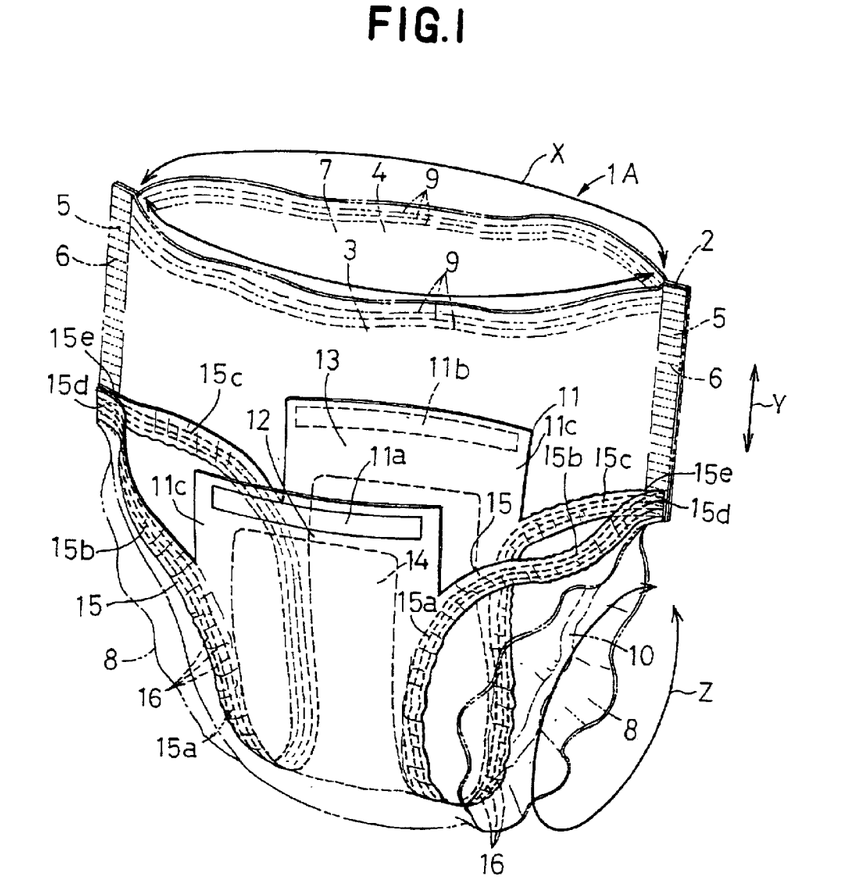
FIG. 1 is a perspective view of an article wherein a pant member are indicated by chain lines.
Figure 2:
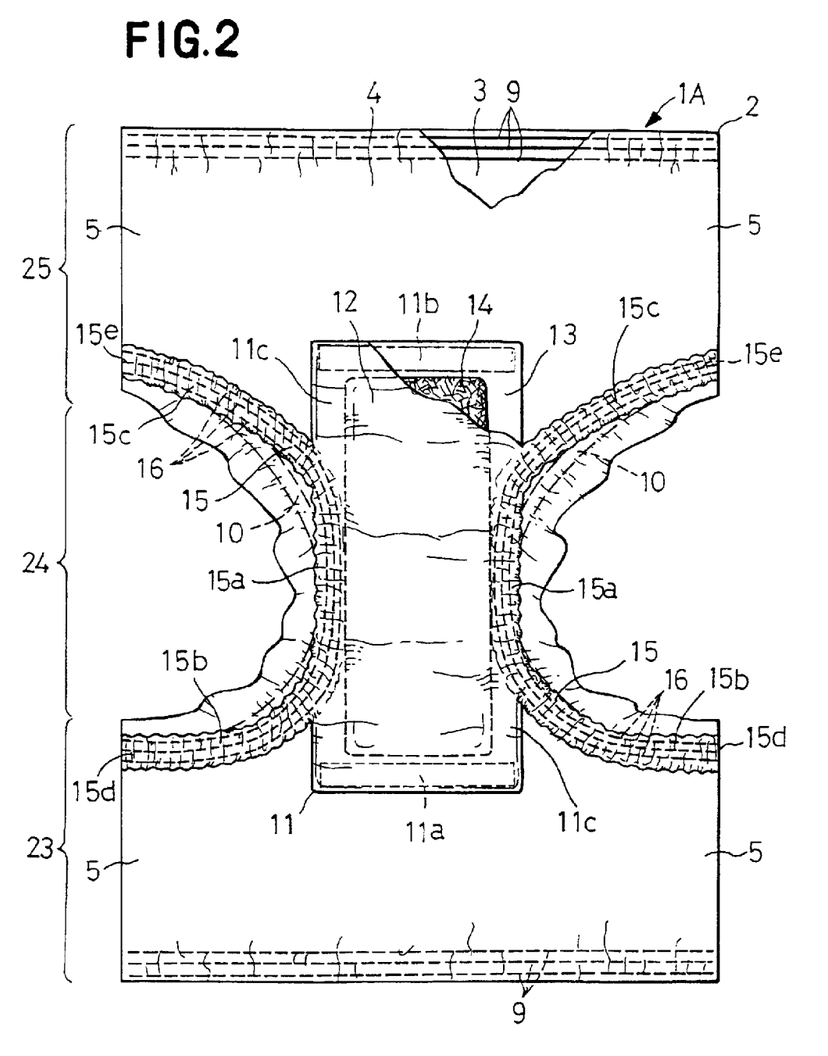
FIG. 2 is a partially cutaway plan view showing the article of FIG. 1 as it has been developed.
Figure 3:
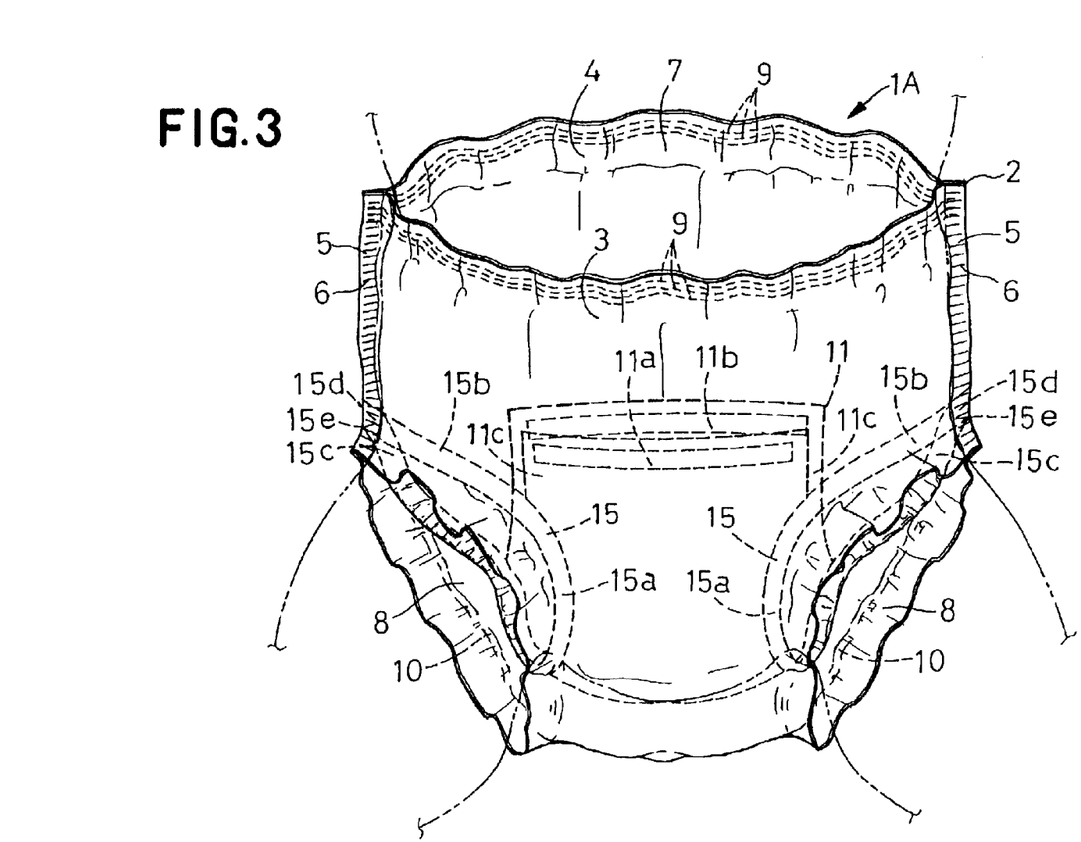
FIG. 3 is a perspective view showing the article in place on a wearer's body.

FIG. 1 is a perspective view of a disposable wearing article 1A wherein pants portion is indicated by chain lines, FIG. 2 is a plan view showing the article 1A of FIG. 1 developed after front and rear waist regions 23, 25 are disconnected from each other and partially cutaway, and FIG. 3 is a perspective view showing the article 1A of FIG. 1 in place on a wearer's body. In FIG. 1, a circumferential direction of the waist region is indicated by an arrow X, a longitudinal direction of it is indicated by an arrow Y, and a circumferential direction of a leg-hole is indicated by an arrow Z. Inner surfaces of top- and backsheets 12, 13 are the surfaces facing a core 14 and outer surfaces of these sheets 12, 13 are the surfaces facing away from the core 14.

A pant member 2 comprises a pair of substantially liquid-impervious sheets 3, 4 overlaid each other and has an hourglass-shape as viewed in its plan view. The pant member 2 is composed of front waist region 23, a rear waist region 25 opposed to the front waist region 23 and a crotch region 24 positioned between these front and rear waist regions 23, 25. In the pant member 2, transversely opposite side edge portions 5 of the front and rear waist regions 23, 25 extending in a longitudinal direction, are overlaid and joined together by means of plural heat-sealing lines 6 arranged intermittently in the longitudinal direction along the side edge portions 5 so as to define a waist-hole 7 and a pair of leg-holes 8.

Along a peripheral edge region of the waist-hole 7, a plurality of elastic members 9 extending in the circumferential direction of the waist-hole 7 are secured under extension to the peripheral edge region. Similarly, peripheral edge regions of the respective leg-holes 8, ribbon-like elastic members 10 extending in the circumferential direction of the leg-holes 8 are secured under extension to these peripheral edge regions. Both the elastic members 9 associated with the waist-hole 7 and the elastic members 10 associated with the leg-holes 8 are interposed between the sheets 3, 4 constituting the pant member 2 and secured to these sheets 3, 4.

A pad member 11 comprises the liquid-pervious topsheet 12, the liquid-impervious backsheet 13 and the liquid-absorbent core 14 disposed between these sheets 12, 13. The core 14 is joined to the inner surface of at least one of the top- and backsheets 12, 13.

The pad member 11 lies in the crotch region 24 of the pant member 2 and further extends into the front and rear waist regions 23, 25. The pad member is delineated by front and rear ends 11a, 11b extending in the circumferential direction of the front and rear waist region and transversely opposite side edges 11c extending in the longitudinal direction between the front and rear ends 11a, 11b. The pad member 11 is provided along its transversely opposite side edges 11c with a pair of elastic thigh-tightening bands 15 extending in the circumferential direction of the respective legs.

The pad member 11 has its front end 11a connected to the front waist region 23 of the pant member 2 and its rear end 11b connected to the rear waist region 25 of the pant member 2. Along the front and rear ends 11a, 11b, the outer surface of the backsheet 13 is bonded to the sheet 4 of the pant member 2.

Each of the thigh-tightening bands 15 is formed by the top- and backsheets 12, 13 of the pad member 11 and has a middle zone 15a lying in the crotch region 24 of the pant member 2 and connected to a middle zone of the side edge 11c of the pad member, and first and second free zones 15b, 15c separated from the side edge 11c of the pad member. Each of the thigh-tightening bands 15 is provided with a plurality of elastic members 16 extending in the circumferential direction of the leg and secured under extension thereto. These elastic members 16 are disposed between the top- and backsheets 12, 13 and secured to respective inner surfaces of the sheets 12, 13.

Each of the first free zones 15b of the thigh-tightening bands 15 lies on the side of the front end 11a of the pad member 11 extending from the side edge 11c toward the side edge 5. Each of the first free zones 15b has its front end 15d connected to the side edge 5 in the vicinity of the leg-hole 8. Each of the second free zones 15c lies on the side of the rear end 11b of the pad member extending from the side edge 11c toward the side edge 5. Each of the second free zones 15c has its rear end 15e connected to the side edge 5 in the vicinity of the leg-hole 8. The middle zone 15a and the first and second free zones 15b, 15c of the thigh-tightening band 15 extend in parallel to the peripheral edge of the leg-opening 8 and substantially define a loop.

Referring to FIG. 2, the respective first free zones 15b extend from the respective side edges 11c of the pad member toward the respective side edges 5 of the front waist region 23 and the front ends 15d of the first free zones 15b are connected to the respective side edges 5 of the front waist region 23 in the crotch region 24. Referring also to FIG. 2, the respective second free zones 15c extend from the respective side edges 11c of the pad member toward the respective side edges 5 of the rear waist region 24 and the rear ends 15e of the second free zones 15c are connected to the respective side edges 5 of the rear waist region 25 in the crotch region 24. Along the front ends 15d of the first free zones 15b and the rear ends 15e of the second free zones 15c, the outer surface of the backsheet 13 of the thigh-tightening bands 15 is secured to the sheet 4 of the pant member 2.

To wear the article 1A, a wearer's legs are first put through the waist-hole 7, then through the loops defined by the respective thigh-tightening bands 15, through the leg-holes 7 of the pants 2 and thereafter the pant member 2 are pulled up along the waist region.

With the article 1A put on a wearer's body, the thigh-tightening bands 15 encircle the wearer's thighs in close contact with them so as to fix the pad member to the wearer's crotch region. In consequence, back-and-forth as well as right- and leftward movement of the pad member 11 in the wearer's crotch region due to the wearer's movement is restricted. In this way, bodily discharges such as urine and feces can be reliably absorbed and contained by the pad member 11 and it is unlikely that bodily discharges might leak from the article 1A in the wearer's crotch region.

Figure 4:
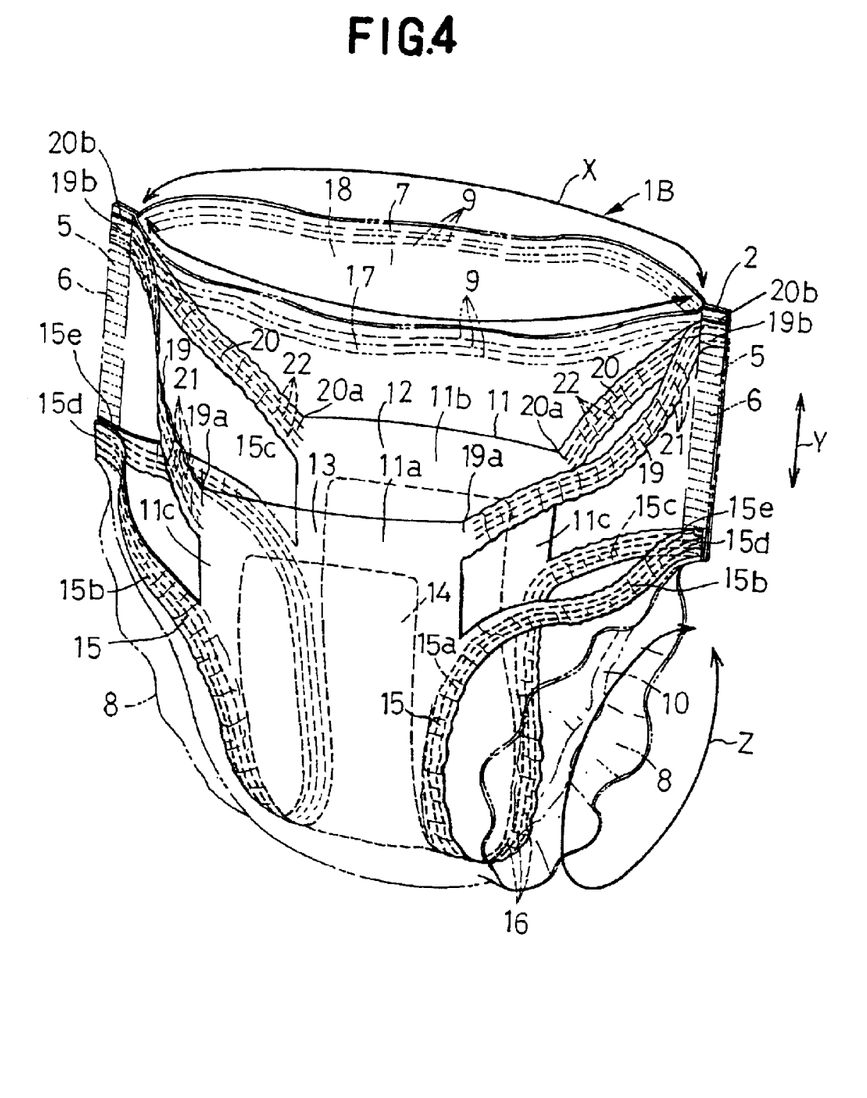
FIG. 4 is a view similar to FIG. 1 but showing another embodiment wherein the pant member are indicated by chain lines.
Figure 5:
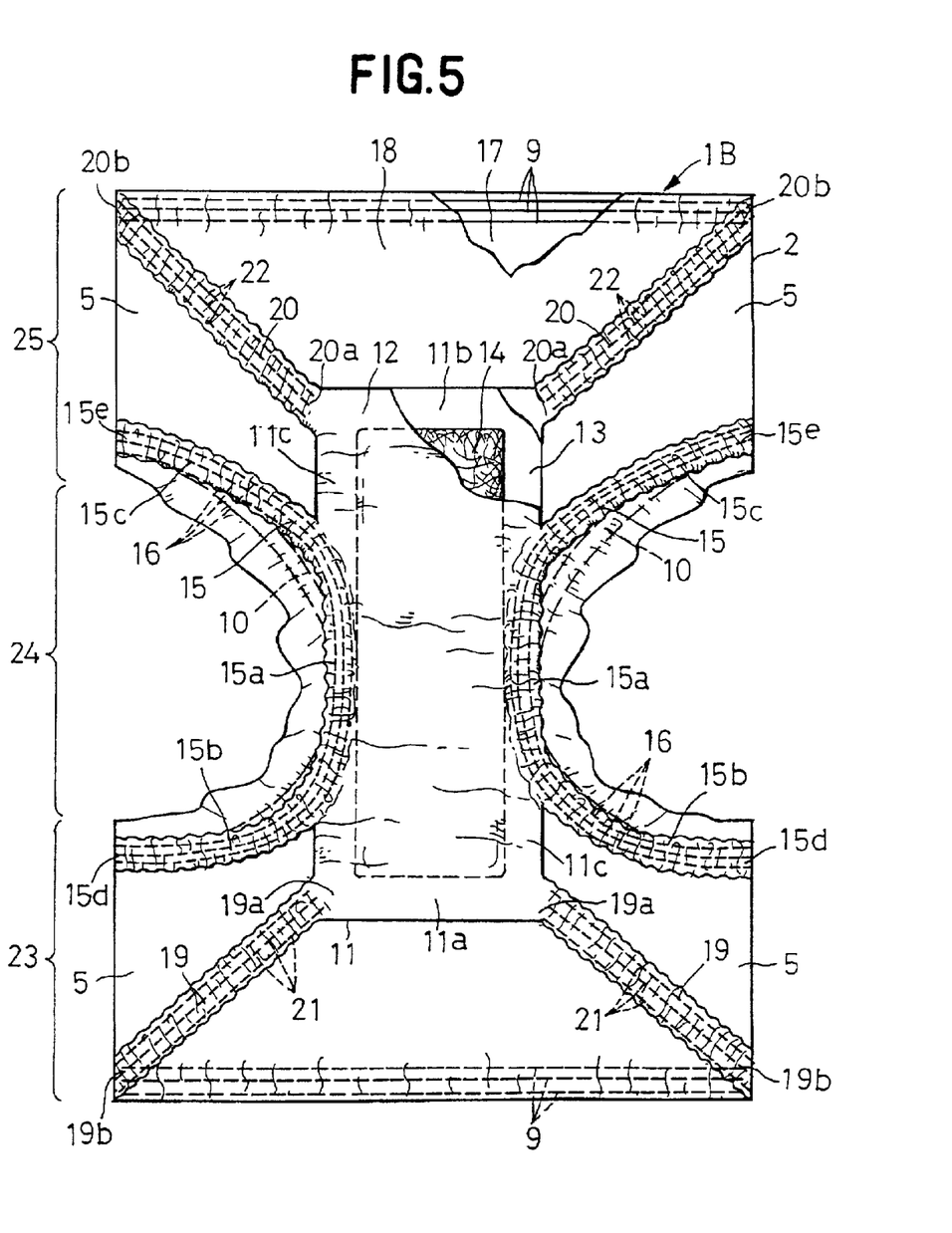
FIG. 5 is a view similar to FIG. 2 but showing the article of FIG. 4 as it has been developed and partially cutaway.
Figure 6:
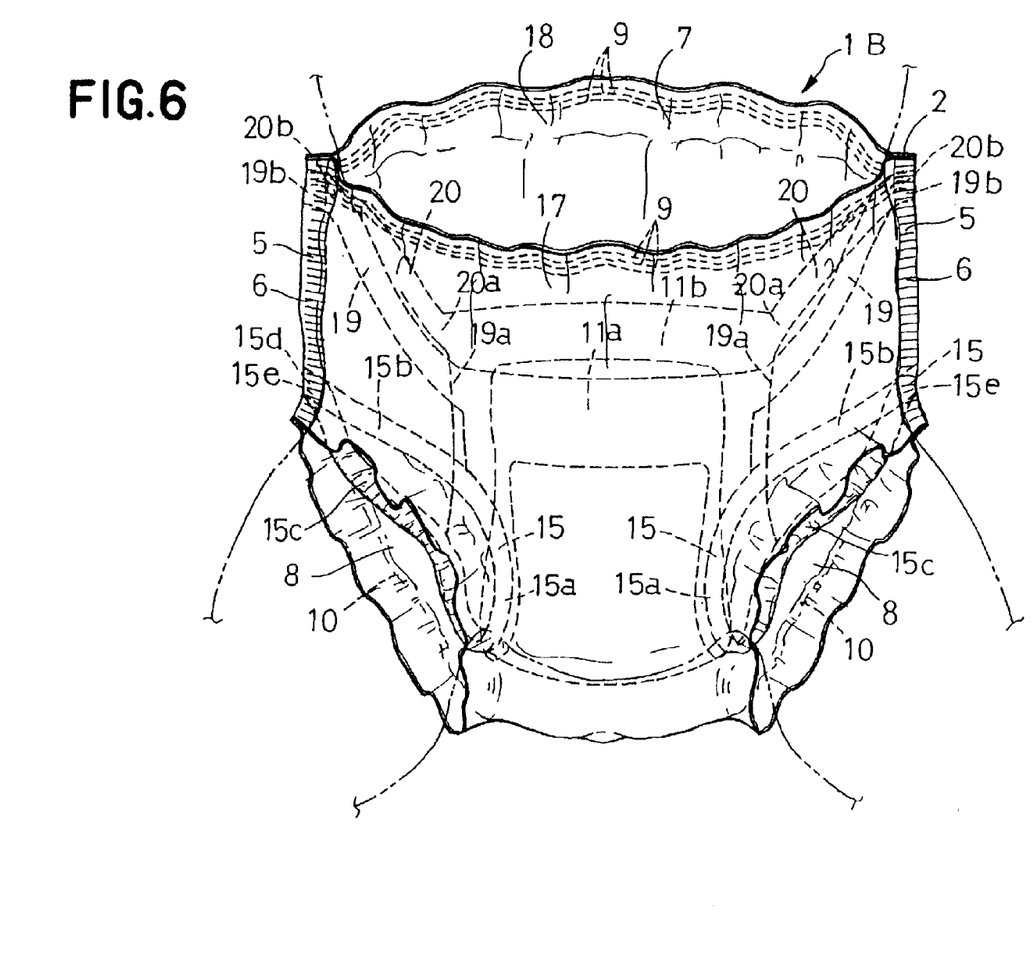
FIG. 6 is a view similar to FIG. 3 showing the article in place on a wearer's body.

FIG. 4 is a view similar to FIG. 1 but showing another disposable wearing article 1B according to another embodiment wherein the pant member as indicated by chain lines, FIG. 5 is a view similar to FIG. 2 but showing the article 1B of FIG. 4 as its front and rear waist regions 23, 25 are disconnected from each other, then flatly developed and partially cutaway and FIG. 6 is a view similar to FIG. 3 showing the article 1B of FIG. 4 as put on a wearer's body. This article 1B is similar to that of FIG. 1 in that the article 1B comprises the pant member 2, the body fluid absorbent pad member 11 lying on the inner side of the pant member 2 and a pair of elastic thigh-tightening bands 15 extending in the circumferential direction of the respective legs. The article 1B is distinguished from the article 1A of FIG. 1 in the following points described below.

In this article 1B, the pad member has a pair of elastic first suspender bands 19 and a pair of elastic second suspender bands 20 so that the pad member may be connected to the pant member 2 by means of these suspender bands 19, 20. In the case of the article 1B, the front and rear ends 11a, 11b of the pad member are not connected to the front and rear waist regions 23, 25 of the pant member 2.

The pant member 2 comprises a pair of substantially liquid-impervious and elastic sheets 17, 18 overlaid each other and have an hourglass-shape as viewed in its plan view. The peripheral edge region of the waist-hole 7 is provided with a plurality of the elastic members 9 secured under extension thereto. Similarly, the peripheral edge regions of the respective leg-holes 8 are respectively provided with ribbon-like elastic members 10 secured under extension thereto.

The first and second suspender bands 19, 20 are respectively formed by the top- and backsheets 12, 13 constituting the pad member 11. These suspender bands 19, 20 are respectively provided with a plurality of elastic members 21, 22 extending in the circumferential direction of the thighs and secured under extension thereto. The elastic members 21, 22 are interposed between the top- and backsheets 12, 13 and secured to the inner surfaces of the sheets 12, 13.

The first suspender bands 19 extend from both sides of the front end 11a of the pad member 11 toward the side edges 5 of the waist region. The first suspender bands 19 have proximal ends 19a connected to both sides of the front end 11a of the pad member and front ends 19b connected to the side edges 5 of the waist region in the vicinity of the waist-hole 7.

The second suspender bands 20 extend from both sides of the rear end 11b of the pad member toward the side edges 5 of the waist region. The second suspender bands 20 have proximal ends 20a connected to both sides of the rear end 11b of the pad member and the rear ends 20b connected to the side edges 5 of the waist region in the vicinity of the waist-hole 7.

Referring to FIG. 5, the first suspender bands 19 lie in a frontal upper pant of the first free zones 15b of the thigh-tightening bands 15 when worn and extend toward the side edges 5 of the waist region in the front waist region 23 and the front ends 19b are connected to the side edges 5 of the waist region on the end of the front waist region 23. The second suspender bands 20 lie in an upper pant of the second free zones 15c of the thigh-tightening bands 15 when worn and extend toward the side edges 5 of the waist region in the rear waist region 25 and the rear ends 20b are connected to the side edges 5 of the waist in the rear waist region 25. At the front ends 19b of the first suspender bands 19 and the rear ends 20b of the second suspender bands 20, the outer surface of the backsheet 13 forming these bands 19, 20 is secured to the sheet 18 forming the pant member 2.

In this article 1B, the pad member is suspended inside the pant member portion 2 by the suspender bands 19, 20 so that, in the crotch region 24 of the pant member 2, the pad member may be pulled up from inside the pant member 2 toward the waist-hole 7. In the article 1B, the pad member 11 may be kept in close contact with the wearer's skin in his or her crotch region. In the case of this article 1B also, even if the pant member 2 is displaced due to the wearer's movement, the pad member may not be easily displaced from its proper position to, for instance, back-and-forth or right- and leftward direction relative to the wearer's crotch region because the pad member is fixed to the wearer's skin in his or her crotch region by the thigh-tightening bands 15. In this way, the article 1B ensures to hold the pad member 11 in close contact with the wearer's skin in his or her crotch region and to enable the pad member 11 to reliably absorb and retain bodily discharges such as urine and feces.

In the article 1B according to this embodiment, the distal ends or front and rear ends 15d, 15e of the first and second free zones 15b, 15c of the respective thigh-tightening bands 15 as well as the front and rear ends 19b, 20b of the first and second suspender bands 19, 20 are connected to the side edges 5. Accordingly, the elasticity of the front and rear waist regions 23, 25 except the side edges 5 thereof is not reduced by these bands so that the elasticity of the pant member 2 can be effectively utilized to fit the article 1B around the wearer's waist region.

The topsheet 12 may be formed using a hydrophilic fibrous nonwoven fabric or a finely apertured plastic film. The backsheet 3 may be formed using a hydrophobic fibrous nonwoven fabric, a liquid-impervious plastic film, double layered hydrophobic fibrous nonwoven fabric overlaid each other, or a composite sheet consisting of a hydrophobic fibrous nonwoven fabric and a plastic film bonded to this fibrous nonwoven fabric.

As a stock material for the sheets 3, 4 as well as the backsheet 13 forming the pant member 2 of FIG. 1, it is also possible to use a composite nonwoven fabric made of a highly water-resistant nonwoven fabric by melt blown process sandwiched by two layers of a spun bond fibrous nonwoven fabric being high in strength as well as in flexibility.

The nonwoven fabric may be selected from those made by spun lacing-, needle punching-, melt blowing-, thermal bonding-, spun bonding-, chemical bonding and air-through processes. The component fiber for the nonwoven fabric may be selected from a group of materials consisting of polyolefine-, polyester- and polyamide-based fibers, and core-sheath-type conjugated fiber or side-by-side-type conjugated fiber of polyethylene/polypropylene or polyethylene/polyester.

The articles 1A, 1B have been illustrated and described in which the thigh-tightening bands 15 as well as the first and second suspender bands 19, 20 are formed by the top- and backsheets 12, 13 forming the pad member 11, i.e., contiguous to the pad member. However, it is also possible to form these bands 15, 19, 20 using a sheet provided separately of the pad member 11. In this case, the middle zones 15a of the thigh-tightening bands 15 will be connected to the side edges 11c of the pad member 11 at middle zones thereof and the proximal ends 19a, 20a of the first and second suspender bands 19, 20 are connected to the front and rear ends 11a, 11b of the pad member 11 at both sides of these respective ends 11a, 11b.

To form these bands 15, 19, 20 using a separately prepared sheet, it is preferred to use a sheet material corresponding to the backsheet 13 provided with the elastic member secured under extension thereto or a suitable elastic sheet material.

The sheet 17, 18 forming the pant member 2 and the elastic sheet forming these bands 15, 19, 20 may be selected from a group of materials consisting of an elastic and hydrophobic fibrous nonwoven fabric, an elastic and liquid-impervious plastic film, a double layered elastic and hydrophobic fibrous nonwoven fabric and a composite sheet made of an elastic and hydrophobic fibrous nonwoven fabric and a liquid-impervious plastic film laminated upon each other.

The elastic fibrous nonwoven fabric may be selected from those made by melt blowing process and spun bonding process. The component fiber for this elastic nonwoven fabric may be elastic fiber obtained by melt spinning a thermoplastic elastomer resin. Alternatively, a hydrophobic fibrous nonwoven fabric made of melt spun crimped fiber of thermoplastic synthetic resin such as polypropylene, polyethylene or polyester may be bonded to at least one surface of a hydrophobic fibrous nonwoven fabric made of thermoplastic elastomer resin fiber to obtain a composite nonwoven fabric as the elastic fibrous nonwoven fabric useful for this invention.

For the article 1A of FIG. 1, the pant member 2 may be formed by the elastic sheet 17, 18 just as well as for the article 1B of FIG. 4. For the article 1A of FIG. 1, it is not essential that the front and rear ends 11a, 11b of the pad member are connected to the front and rear waist regions 23, 25 of the pant member 2.

While the articles 1A, 1B have been illustrated and described as the side edges 5 of the front and rear waist regions 23, 25 were previously joined together to form the pant member 2, this invention is applicable also to an open-type article in which the front and rear waist regions 23, 25 are connected to each other just before the articles are worn. In the case of the open-type article, a pair of tape fasteners are attached to the side edges 5 of the rear waist region 25 and a target tape strip serving as a landing zone for these tape fasteners are attached to the outer surface of the sheet 3, 17 in the front waist region 23. With the pant member 2 of the open-type article, free ends of the respective tape fasteners are anchored on the target tape strip and thereby the front and rear waist regions 23, 25 are connected to each other to define the waist-hole 7 and the pair of leg-holes 8.

The core 14 is a mixture of fluff pulp and super-absorbent polymer particles or a mixture of fluff pulp, super-absorbent polymer particles and thermoplastic synthetic resin fiber both compressed to a desired thickness. Preferably, the core 14 is entirely covered with tissue paper to prevent the polymer particles from falling off and/or to prevent the core 14 from being deformed in shape. The polymer particles may be selected from a group consisting of starch-, cellulose- and synthetic polymer-based particles.

Bonding of the top- and backsheets 12, 13, the thigh-tightening bands, the first and second suspender bands 19, 20, the elastic members 9, 10, 16, 21, 22 and the core 14 may be achieved by applying a hot melt adhesive or welding technique such as heat-sealing or ultrasonic welding.

With the disposable wearing article according to this invention put on a wearer's body, the elastic thigh-tightening bands surround the wearer's thighs in close contact therewith so that the pad may be fixed in the wearer's crotch region by these thigh-tightening bands. Even if the pants shifts due to movement of the wearer, the pad is well resistant against any significant position shift in the wearer's crotch region back-and-forth as well as right- and leftward. In this way, the article according to this invention ensures that bodily discharges such as urine and feces can be reliably absorbed and contained by the pad without any apprehension that bodily discharges might leak from the wearer's crotch region.

In the case of the article provided with, in addition to the first and second tightening bands, the elastic first and second suspender bands, the pad is suspended inside the pant member by these suspender bands so that, in the crotch region, the pad is pulled up toward the waist-hole so that the pad member may be maintained in close contact with the wearer's skin in his or her crotch region. In this way, the article ensures that the pad can reliably absorb and retain bodily discharges such as urine and feces.

What is claimed is:
1. A disposable wearing article comprising:
   a pant member having front and rear waist regions opposed to each other and a crotch region;
   transversely opposite side edge portions of said waist regions being overlaid and joined together so as to define a waist-hole and a pair of leg-holes, and
   a body fluid absorbent pad member lying inside said pant member and extending from said crotch region into said front and rear waist regions;
   said disposable wearing article further comprising:
   said pad member having front and rear ends and transversely opposite side edges and a pair of elastic thigh-tightening bands;
   said thigh-tightening bands respectively having middle zones lying in the crotch region of said pant member and connected to side edges of said pad member, first free zones lying on a side of a front end of said pad member and extending toward side edges of the waist region and second free zones lying on a side of a rear end of said pad member and extending toward the side edges of said waist region; and
   front ends of said first free zones and rear ends of said second free zones are connected to the side edges of said waist region in vicinity of said leg-holes of said pant member while the middle zones and first and second free zones of said thigh-tightening bands extend generally parallel to respective said leg-holes of said pant member so as to substantially form loops.
2. The article according to claim 1, wherein the front and rear ends of said pad member are connected to the front and rear waist regions of said pant member.
3. The article according to claim 1, wherein said pad member has a pair of elastic first suspender bands extending from both sides of its front end toward the side edges of said waist region and a pair of elastic second suspender bands extending from both sides of its rear end toward the side edges of said waist region and wherein front ends of said first suspender bands and rear ends of said second suspender bands are connected to the side edges of said waist region in vicinity of the waist-hole of said pant member.
4. The article according to claim 1, wherein said pant member is formed of a substantially liquid-impervious sheet and said pad member is formed of a liquid-pervious topsheet, a liquid-impervious backsheet and a liquid-absorbent core interposed therebetween.

* * * * *